(12) United States Patent
Chen

(10) Patent No.: US 9,168,220 B2
(45) Date of Patent: Oct. 27, 2015

(54) EYE CREAM AND PREPARATION METHOD

(75) Inventor: Ping Chen, Wuhan (CN)

(73) Assignee: MAYINGLONG PHARMACEUTICAL GROUP CO., LTD, Wuhan (CN)

( * ) Notice: Subject to any disclaimer, the term of this patent is extended or adjusted under 35 U.S.C. 154(b) by 511 days.

(21) Appl. No.: 13/390,679

(22) PCT Filed: May 3, 2011

(86) PCT No.: PCT/CN2011/073612
§ 371 (c)(1),
(2), (4) Date: Feb. 15, 2012

(87) PCT Pub. No.: WO2011/153880
PCT Pub. Date: Dec. 15, 2011

(65) Prior Publication Data
US 2012/0148680 A1 Jun. 14, 2012

(30) Foreign Application Priority Data

Jun. 12, 2010 (CN) .......................... 2010 1 0199305

(51) Int. Cl.
| | |
|---|---|
| *A61Q 19/08* | (2006.01) |
| *A61K 8/98* | (2006.01) |
| *A61K 8/19* | (2006.01) |
| *A61K 8/27* | (2006.01) |
| *A61K 8/35* | (2006.01) |
| *A61K 8/67* | (2006.01) |
| *A61K 8/34* | (2006.01) |
| *A61Q 19/00* | (2006.01) |

(52) U.S. Cl.
CPC . *A61K 8/987* (2013.01); *A61K 8/19* (2013.01); *A61K 8/27* (2013.01); *A61K 8/34* (2013.01); *A61K 8/35* (2013.01); *A61K 8/678* (2013.01); *A61Q 19/005* (2013.01); *A61Q 19/08* (2013.01); *A61K 2800/31* (2013.01)

(58) Field of Classification Search
None
See application file for complete search history.

(56) References Cited

U.S. PATENT DOCUMENTS

2009/0155383 A1* 6/2009 Kitko et al. .................... 424/642

FOREIGN PATENT DOCUMENTS

| CN | 1931125 A | 3/2007 |
|---|---|---|
| CN | 100571737 C | 12/2009 |
| CN | 101849898 B | 1/2012 |
| CN | 102578074 B | 3/2013 |
| CN | 103690468 A | 4/2014 |

OTHER PUBLICATIONS http://pubchem.ncbi.nlm.nih.gov/compound/Tocopherol_acetate#section=Synonyms, Accessed Dec. 31, 2014.*
http://www.ncbi.nlm.nih.gov/mesh/68024502, Accessed Dec. 31, 2014.*
Wang Yangqin, Yang Weihua, Zhou Dayun, Kuang Meng, Fang Dan, Ma Lei, Research of the Extraction Process of Cottonseed Oil VE, Cotton Research Institme, Chinese Acadamy of Agricuhural Science, Anyang Henan 45512, Chinese Agricultural Science Bulletin, 2014,30(27):288-292.
Huang Kai Qin Xi Huan Cheng Yuan Jiang Qing Huang Xiuyun Liu Kang Ultra, Vitamin E and selenium on reproductive hormones And immune function, ( Animal Science and Technology , Guangxi University, Nanning 530004, China : 2 Feed Group Co., Ltd. Guangdong Guangdong , Zhanjiang 524001), 2013 vol. 34 24 Total No. 453.
Juan Yan, Jun Liu, Li Yung, Yan-Yan Pan, Li Zheng, Ya-Ming Cao, Vitamin E Inhibits Immune Responses During The Early Stage of P. y 17XL Infenction in BALB/c Mice, Department of Immunology, College of Basic Medical Sciences, China Mediacal University, Shenyang 110001, China, Chinese books CLC 11328.3 Document code A Article ID 1000-484X (2012) 12.1125-04, p. 1125.
Zhu Qiu-Hang, Huang Jin-Xiang, Meng Cong-Shen, Experimental Study on Therapeutic Effiacy of tetrandine combined with Vitamin E Against Acute Toxicity of Paraquat, (National Institute of Occupational Health and Poison Control, Chinese Center for Disease Control and Prevention, Beijing100050, China, 1002—221X(2014)05—0329—04 DOI : 10. 13631/j. cnki. zggyyx. 2014. 05. 00, Chinese J Ind Med Oct. 2014, vol. 27 No. 5, p. 329.
Fathi, Mokhtar; ADL, Kambiz Nazer; Nezhad, Yahya Ebrahim, The Effects Of Vitamin E And L-Arginine Supplementation On Antioxidant Status And Biochemical Indices Of Broiler Chickens With Pulmonary Hypertension Syndrome, Journal of Animal and Veterinary Advances vol. 11 Issue2 158-164, 7 pp. Journal; Online Computer File 2012 CODEN:JAVAB3 ISSN:1993-601X.
Truska, Jaroslav; Dong, Lan-Feng; Rohlena, Jakub; Stursa, Jan; Vondrusova, Magdalena; Goodwin, Jacob; Nguyen, Maria; Kluckova, Katarina; Rychtarcikova, Zuzana; Lettlova, Sandra; Spacilova, Jana; Stapelberg, Michael; Zoratti, Mario; Neuzil, Jiri , Mitochondrially Targeted Vitamin E Succinate Modulates Expression Of Mitochondrial Dna Transcripts And Mitochondrial Biogenesis, Antioxidants & Redox Signaling Vol.22 Issue11 pp. 883-900 Journal; Online Computer File 2015 CODEN:ARSIF2 ISSN:1523-0864 DOI:10.1089/ars.2013.5594.
Hategekimana, Joseph; Chamba, Moses. V. M.; Shoemaker, Charles F.; Majeed, Hamid; Zhong, Fang, Vitamin E Nanoemulsions By Emulsion Phase Inversion: Effect Of Environment Stress And Long-Term Storage On Stability And Degradation In Different Carrier Oil Types, Colloids and Surfaces, A: Physicochemical and Engineering Aspects PagesAhead of Print, Journal 2015, CODEN:CPEAEH, ISSN:0927-7757, DOI:10.1016/j.colsurfa.2015.03.020.

* cited by examiner

*Primary Examiner* — Peter J Reddig
*Assistant Examiner* — Sarah Chickos
(74) *Attorney, Agent, or Firm* — Maschoff Brennan

(57) ABSTRACT

An eye cream comprises the following components: 2-16 parts of pearl, 0.2-2 parts of borax, 10-28 parts of VE, 0.005-0.05 parts of muscone, 0.2-3 parts of borneol, 30-90 parts of eye circles 338Y324 and 0.05-2 parts of zinc carbonate hydroxide in weight. The eye cream has good effects of increasing moisture, continuously locking water, inhibiting melanin, increasing the skin brightness and the skin texture.

5 Claims, 11 Drawing Sheets

EYE CREAM AND PREPARATION METHOD

TECHNICAL FIELD OF THE INVENTION

The invention relates to an eye cream and preparation method of it.

BACKGROUND OF THE INVENTION

The skin of the eyelid is the thinnest in the whole human body. The skin is most prone to aging, thereby telling the story of people's true age. Generally, eye skin aging always accompanies with eye pouches, black eye circles and crow's feet, which are caused by internal physiological changes such as blood circulation slowdown and inadequate oxygen supply, and some external factors such as UV ray stimulation or the like. The formation of eye pouch is mainly due to eye skin and muscle relaxation with increase of age or eye overfatigue such as sleep insufficiency and long-term working under computer circumstances. The black eye circle means that the eyelids in eye sockets exhibit a darker color, and is associated with the number of pigments of eyelid itself, vessel blood flow within the eyelid and other factors. There are many reasons for the formation of the black eye circle, which mainly include that (1) the black eye circle is caused by sleep insufficiency, nutrient deficiency, eye fatigue, unhealthy lifestyle and cosmetics pigmentation; (2) the black eye circle is caused by pigments deposited in the eye due to changes in body hormones during menstruation, in the late period of pregnancy or after childbirth; (3) the black eye circle is caused by qi and blood imbalance, and blood stasis block resulted from inadequate blood supply and bad venous return of subcutaneous tissue around the eyes of patients suffering from the high blood pressure, diabetes, kidney disease, liver disease and the weak suffering from long illness.

Now, there are many eye care products on the market, which are of single function. Most of these products are daily moisturizing. Artificially synthesized nutrient component is the main component of these products, so the cost is high. The application of traditional Chinese medicine to cosmetics, skin care products and health care products has a long history, but an eye cream, the main component of which is the traditional Chinese medicine, and which has the comprehensive effects of removing black eye circles, eye pouches, wrinkles or the like, has not been reported before.

SUMMARY OF THE INVENTION

In order to solve the above technical problem, the invention provides an eye cream and preparation method thereof.

The eye cream provided by the invention comprises the following components in part by weight:
  2-16 parts of pearl
  0.2-2 parts of borax
  10-28 parts of Vitamin E (VE)
  0.005-0.05 parts of muscone
  0.2-3 parts of borneol
  30-90 parts of complexe contour des yeux 338Y324
  0.05-2 parts of zinc carbonate hydroxide.

Further, the eye cream also comprises the following components in part by weight:
  470-700 parts of de-ionized water
  45-75 parts of propylene glycol
  10-40 parts of cetearyl alcohol
  20-45 parts of petrolatum
  6-25 parts of glyceryl stearate
  40-64 parts of glycerol
  7-30 parts of polyacrylamide As a preference, the eye cream also comprises the following components in part by weight:
  0.1-1 parts of disodium EDTA
  0.2-10 parts of methyl hydroxybenzoate
  70-120 parts of cyclomethicone
  18-40 parts of polydimethylsiloxane
  0.05-2 parts of propyl hydroxybenzoate
  1-14 parts of citric acid
  1-5 parts of DMDM hydantoin (SPG)
  0.6-3 parts of essence
  1-8 parts of polysorbate-20
  1-15 parts of polysorbate-60

The invention claims a method for preparing the eye cream, comprising the following steps:

(1) pulverizing pearl and borax respectively, mixing with basic zinc carbonate after sieving with a 100 mesh sieve, grinding and sieving with a 160 mesh sieve, pulverizing mixed powder to 200 mesh by airflow;

(2) homogenizing the mixed powder obtained in Step (1) with the glycerol and mixing them uniformly;

(3) taking said amount of de-ionized water and 40~60 parts by weight of propylene glycol, adding them into a homogeneous boiler orderly, uniformly dispersing, heating to 78° C. and preserving heat for subsequent use;

(4) taking said amount of cetearyl alcohol, white vaseline and glyceryl stearate, adding them into a boiler orderly, heating to 78° C., adding the mixture obtained in Step (2) into the boiler, and uniformly dispersing;

(5) adding the mixture obtained in Step (4) into the mixture obtained in Step (3), homogenizing them, mixing uniformly and cooling;

(6) adding said amount of polyacrylamide into the mixture obtained in Step (5) while cooling it to 70° C., vacuumizing them, homogeneously stirring uniformly and cooling;

(7) cooling the mixture obtained in Step (6) to 50° C., adding said amount of VE, muscone, propylene glycol solution of borneol and complexe contour des yeux 338Y324 into the mixture orderly, homogeneously stirring uniformly, wherein the propylene glycol solution of borneol is obtained by dissolving said amount of borneol in 5-15 parts of propylene glycol;

(8) cooling the mixture obtained in Step (7) to 37-38° C., stirring it uniformly.

The invention further claims a method for preparing the eye cream, comprising the following steps:

(1) pulverizing pearl and borax respectively, mixing with basic zinc carbonate after sieving with a 100 mesh sieve, grinding and sieving with a 160 mesh sieve, pulverizing mixed powder to 200 mesh by airflow;

(2) homogenizing the mixed powder obtained in Step (1) with the glycerol and mixing them uniformly;

(3) taking 457-675 parts by weight of de-ionized water, said amount of disodium EDTA, polysorbate-60 and methyl hydroxybenzoate and 40~60 parts by weight of propylene glycol, adding them into a homogeneous boiler orderly, uniformly dispersing, heating to 78° C. and preserving heat for subsequent use;

(4) taking said amount of polydimethylsiloxane, cetearyl alcohol, white vaseline, glyceryl stearate, cyclomethicone and propyl hydroxybenzoate, adding them into a boiler orderly, heating to 78° C., adding the mixture obtained in Step (2) into the boiler, and uniformly dispersing;

(5) adding the mixture obtained in Step (4) into the mixture obtained in Step (3), homogenizing them, mixing uniformly and cooling;

(6) adding said amount of polyacrylamide into the mixture obtained in Step (5) while cooling it to 70° C., vacuumizing them, homogeneously stirring uniformly and cooling;

(7) adding said amount of citric acid and 8-15 parts of de-ionized water into the mixture obtained in Step (6) while cooling it to 60° C., vacuumizing them, homogeneously stirring uniformly and cooling;

(8) cooling the mixture obtained in Step (7) to 50° C., adding said amount of VE, muscone, propylene glycol solution of borneol and complexe contour des yeux 338Y324 into the mixture orderly, homogeneously stirring uniformly, cooling, wherein the propylene glycol solution of borneol is obtained by dissolving said amount of borneol in 5-15 parts of propylene glycol;

(9) adding said amount of DMDM hydantoin, 5-10 parts by weight of de-ionized water, said amount of essence and said amount of polysorbate-20 into the mixture obtained in Step (8) while cooling it to 40° C., homogeneously stirring uniformly;

(10) cooling the mixture to 37-38° C., stirring it uniformly.

The technical scheme provided by the invention can achieve the following technical effects:

1. The main components in the formula are prepared by a superfine pulverization technology of traditional Chinese medicine to micronize the medicine, which is easy to penetrate through skin and mucosa. The main effective components have remarkable effects, and at the same time improve the appearance quality of the skin care product.

2. The eye cream of the invention is not greasy, easy to spread and comfortable to use.

3. The addition of the disodium EDTA, methyl hydroxybenzoate, cyclomethicone, polydimethylsiloxane, propyl hydroxybenzoate, citric acid, DMDM hydantoin (SPG), essence, polysorbate-20 and polysorbate-60 can significantly improve the luster, lightness, viscosity and other appearance indexes of the eye cream to make the eye cream moister, easy to spread and make the skin feels pleasant after use.

4. The test result of efficacy research shows that: the eye cream, after use, has remarkable moisturizing effect, strong moisturizing ability and strong continuous water lock effect, good abilities of inhibiting melanin and increasing skin lightness, and at the same time has the effects of improving skin texture, i.e. delaying skin aging.

5. The toxicology test result shows that: this product has the characteristics of low toxicity, safety and no stimulation. Rabbit acute eye stimulation test result shows that: after 0.1 ml of eye cream of the invention is dropped into the right eyes of the test rabbits, all the test rabbits close their eyes, and there is no obvious secretion, no obvious edema, the results show that the eye cream has no stimulation. Many skin stimulation test results show that: the animal subjects do not exhibit systemic poisoning after continuous administration for 14 days. The skin also has no obvious erythema and edema after stimulation test.

6. The human body stimulation and patch test results show that the eye cream is safe and non-stimulating, and has no adverse reactions to human body. The stimulation test shows that the eye cream (with an addition concentration of $80 \times 10^{-5}$ and $640 \times 10^{-5}$) has no stimulation in an RBC test system. All the subjects in the human body patch test have no adverse reactions, which shows that the eye cream has no adverse reactions to human body.

DETAILED DESCRIPTION OF THE INVENTION

Figure 1:
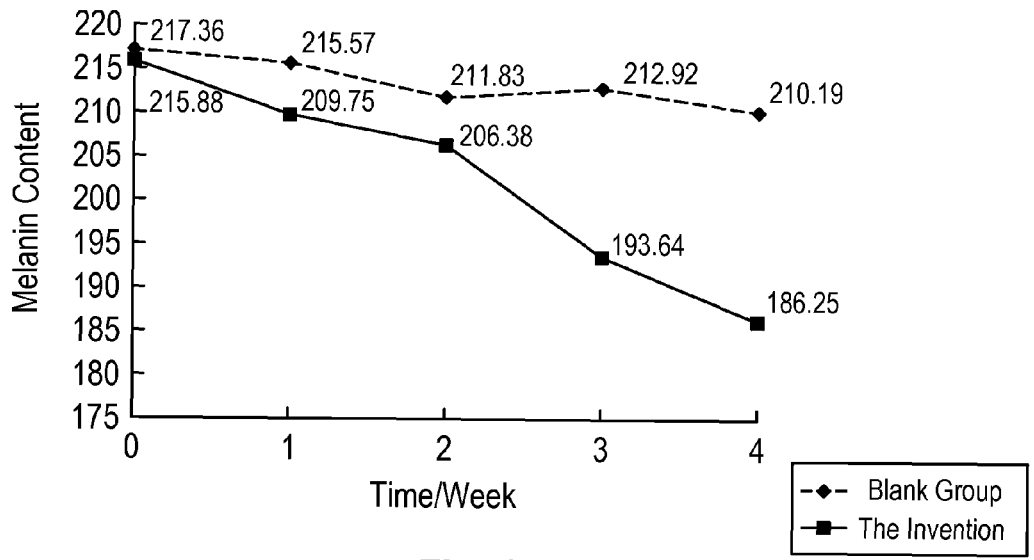
FIG. 1 shows changes of melanin after the invention is used.

The invention is further described below in conjunction with the accompanying drawings and specific embodiments to make those skilled in the art better understand and implement the invention, but the embodiments given shall not limit the invention.

The medicine dosage of the embodiment of the invention is as follows (part by weight):

|  | Embodiments | | | | | | | | | |
| --- | --- | --- | --- | --- | --- | --- | --- | --- | --- | --- |
| Raw materials | 1 | 2 | 3 | 4 | 5 | 6 | 7 | 8 | 9 | 10 |
| De-ionized water | 470 | 500 | 700 | 605.4 | 585.5 | 520.6 | 600 | 640.5 | 510.6 | 535.3 |
| Disodium EDTA | 0.1 | 0.5 | 0.4 | 1 | 0.3 | 0.8 | 0.6 | 0.7 | 0.9 | 0.2 |
| Propylene glycol | 70 | 72 | 75 | 73 | 60 | 45 | 65 | 74 | 50 | 55 |

| Raw materials | 1 | 2 | 3 | 4 | 5 | 6 | 7 | 8 | 9 | 10 |
|---|---|---|---|---|---|---|---|---|---|---|
| Polysorbate-60 | 5 | 10 | 15 | 12 | 8 | 4 | 1 | 2 | 6 | 3 |
| Methyl hydroxybenzoate | 1 | 3 | 4 | 0.2 | 2 | 5 | 10 | 6 | 8 | 0.5 |
| Polydimethylsiloxane | 18 | 20 | 25 | 28 | 32 | 35 | 30 | 35 | 40 | 38 |
| Cetearyl alcohol | 12 | 20 | 40 | 10 | 15 | 30 | 25 | 28 | 22 | 35 |
| Petrolatum (white vaseline) | 40 | 45 | 42 | 30 | 20 | 35 | 32 | 22 | 25 | 28 |
| Glyceryl stearate | 25 | 20 | 15 | 22 | 18 | 8 | 10 | 12 | 6 | 14 |
| Cyclomethicone | 70 | 80 | 120 | 110 | 105 | 95 | 85 | 90 | 88 | 115 |
| Propyl hydroxybenzoate | 0.05 | 1 | 0.1 | 1.5 | 1.2 | 0.5 | 0.8 | 2 | 1.8 | 0.6 |
| Zinc carbonate hydroxide | 0.1 | 0.15 | 0.05 | 2 | 0.25 | 0.2 | 1.5 | 1 | 0.5 | 0.8 |
| Pearl | 8.8 | 10.2 | 16 | 9.5 | 6 | 7.8 | 2 | 5.5 | 9 | 12.5 |
| Borax | 0.5 | 0.2 | 0.8 | 1.2 | 1 | 1.5 | 1.8 | 2 | 1.6 | 0.9 |
| Glycerol | 64 | 60 | 55 | 42 | 53 | 45 | 40 | 48 | 58 | 50 |
| Polyacrylamide | 10 | 15.8 | 18.9 | 25.8 | 20.5 | 30 | 9.8 | 7 | 8.6 | 12.5 |
| Citric acid | 3 | 1 | 5 | 8 | 14 | 10 | 12 | 6 | 7 | 9 |
| VE | 15 | 18 | 10 | 22 | 25 | 19 | 20 | 26 | 28 | 16 |
| Muscone | 0.01 | 0.02 | 0.05 | 0.04 | 0.016 | 0.024 | 0.005 | 0.03 | 0.025 | 0.018 |
| Borneol | 1.25 | 0.2 | 1 | 3 | 2 | 2.5 | 1.8 | 1.5 | 0.5 | 0.8 |
| Complexe contour des yeux 338Y324 (commercial) | 40 | 48 | 50 | 60 | 90 | 80 | 65 | 70 | 82 | 30 |
| DMDM hydantoin (SPG) | 1 | 1.5 | 4 | 3 | 2 | 3.5 | 2.8 | 1.8 | 2.5 | 5 |
| Essence | 0.8 | 1.8 | 1.0 | 0.6 | 2 | 1.5 | 2.2 | 3 | 2.5 | 2.8 |
| Polysorbate-20 | 5 | 2 | 3.5 | 1 | 6 | 6.5 | 7.5 | 5.5 | 4.5 | 8 |

The preparation steps of the eye cream include:

(1) pulverizing pearl and borax respectively, then sieving with a 100 mesh sieve, mixing basic zinc carbonate with the above three medicinal powders, grinding the mixture in a grinding bowl, sieving with a 160 mesh sieve, then pulverizing the mixed powder by airflow;

(2) homogenizing the fine powders of pearl, borax and basic zinc carbonate with the glycerol at a speed of 2000-3000 rpm on a desk homogenizer and mixing them uniformly;

(3) adding 457-675 parts of de-ionized water, disodium EDTA, 40-60 parts of propylene glycol, polysorbate-60 and methyl hydroxybenzoate into a homogeneous boiler orderly, uniformly dispersing, heating to 78° C. and preserving heat for subsequent use;

(4) adding polydimethylsiloxane, cetearyl alcohol, white vaseline, glyceryl stearate, cyclomethicone and propyl hydroxybenzoate into a boiler orderly, heating to 78° C., adding the mixture obtained in Step (2) into the boiler, and uniformly dispersing;

(5) pumping the mixture obtained in Step (4) into the mixture obtained in Step (3) slowly, starting the homogenizer (1150-1250 rpm) and the side-scraping stirrer (400-500 rpm), keeping this speed for 15 minutes, reducing the speed of the homogenizer to 700-900 rpm, the speed of the side-scraping stirrer at 400-500 rpm, and cooling;

(6) adding the polyacrylamide into the mixture while cooling it to 70° C., vacuumizing them (−0.05 Pa), stirring uniformly at the speed of 700-900 rpm of the homogenizer and the speed of 400-500 rpm of the side-scraping stirrer, and cooling;

(7) adding citric acid and 8-15 parts of de-ionized water into the mixture while cooling it to 60° C., reducing the speed of the homogenizer to 700-900 rpm, the speed of the side-scraping stirrer at 400-500 rpm, and cooling;

(8) cooling the mixture to 50° C., adding VE, muscone, propylene glycol solution of borneol (dissolving the borneol in 5-15 parts of propylene glycol solution in advance) and complexe contour des yeux 338Y324 into the mixture orderly, homogeneously stirring at a speed of 700-900 rpm, scraping stirring at a speed of 400-500 rpm uniformly and cooling;

(9) adding SPG, 5-10 parts of de-ionized water, essence and polysorbate-20 into the mixture while cooling it to 40° C., stirring uniformly at the speed of 700-900 rpm of the homogenizer and the speed of 400-500 rpm of the side-scraping stirrer;

(10) stopping the homogenizer, reducing the speed of the side-scraping stirrer to below 400 rpm, cooling to 37-38° C., and stirring uniformly.

In the present invention, the amount of de-ionized water is 470-700 parts. The de-ionized water is added in three steps: 457-675 parts of de-ionized water is added in Step (3); 8-15 parts of de-ionized water is added in Step (7); and 5-10 parts of de-ionized water is added in Step (9). The amount of propylene glycol is 45-75 parts: 40-60 parts of propylene glycol is added in Step (3) and 5-15 parts of propylene glycol is added in Step (8).

The addition of the disodium EDTA, methyl hydroxybenzoate, cyclomethicone, polydimethylsiloxane, propyl hydroxybenzoate, citric acid, DMDM hydantoin (SPG), essence, polysorbate-20 and polysorbate-60 can significantly improve the luster, lightness, viscosity and other appearance indexes of the eye cream to make the eye cream moister, easy to spread and make the skin feel pleasant after use.

Embodiment 11

The eye cream of the invention is prepared by the following components in part by weight:

10 parts of pearl
0.5 parts of borax
20 parts of VE
0.01 parts of muscone
1 part of borneol
50 parts of complexe contour des yeux 338Y324
1 part of zinc carbonate hydroxide 600 parts of de-ionized water
60 parts of propylene glycol
30 parts of cetearyl alcohol
30 parts of petrolatum
15 parts of glyceryl stearate
50 parts of glycerol
20 parts of polyacrylamide.

The preparation method comprises the following steps:

(1) pulverizing pearl and borax respectively, mixing with basic zinc carbonate after sieving with a 100 mesh sieve, grinding and sieving with a 160 mesh sieve, pulverizing mixed powder by airflow;

(2) homogenizing the mixed powder obtained in Step (1) with the glycerol and mixing them uniformly;

(3) taking said amount of de-ionized water and 45 parts by weight of propylene glycol, adding them into a homogeneous boiler orderly, uniformly dispersing, heating to 78° C. and preserving heat for subsequent use;

(4) taking said amount of cetearyl alcohol, white vaseline and glyceryl stearate, adding them into a boiler orderly, heating to 78° C., adding the mixture obtained in Step (2) into the boiler, and uniformly dispersing;

(5) adding the mixture obtained in Step (4) into the mixture obtained in Step (3), homogenizing them, mixing uniformly and cooling;

(6) adding said amount of polyacrylamide into the mixture obtained in Step (5) while cooling it to 70° C., vacuumizing them, homogeneously stirring uniformly and cooling;

(7) cooling the mixture obtained in Step (6) to 50° C., adding said amount of VE, muscone, propylene glycol solution of borneol and complexe contour des yeux 338Y324 into the mixture orderly, homogeneously stirring uniformly, wherein the propylene glycol solution of borneol is obtained by dissolving said amount of borneol in 15 parts of propylene glycol;

(8) cooling the mixture obtained in Step (7) to 37-38° C., stirring it uniformly.

The eye cream has remarkable effects on inhibiting and improving black eye circles, eye pouches and wrinkles, and has the characteristics of safety and no stimulation. Relevant research results are reported as follows:

I. Whitening efficacy evaluation

Method: There are 32 subjects, divided into group A and group B, group A consisting of 16 subjects, 5 males and 11 females, aged from 30 to 60, group B consisting of 16 subjects, 7 males and 9 females, aged from 30 to 60. If adverse reactions are seen in 2 subjects during test, the test is terminated. No adverse reaction is found.

Using time: The volunteers apply the eye cream once in the morning and evening every day.

The invention group refers to the eye skin of a subject who applies the eye cream of any embodiment of the invention, and the blank group refers to the eye skin of a subject who does not apply the eye cream.

(I) Analysis on the Change of Melanin Content

Result: Analysis results are detailed in FIG. 1.

1. The content of melanin in the skin is on a downward trend after the use of the eye cream of the invention.

2. The t test (It is a method for testing the difference degree of two averages. In this method, the probability of occurrence of a difference is inferred based on T distribution theory to judge whether the difference between the two averages is significant.) shows that the content of melanin is obviously lower than that in the blank group ($p<0.05$) after the use of the eye cream of the invention for three weeks.

(II) Data Change of Melanin Relative to Initial Value

Relative change of melanin=(the melanin of the invention group $T_n$–the melanin of the invention group $T_0$)/the melanin of the invention group $T_0$, wherein $T_0$ represents the melanin content value of each subject before test, and $T_n$ represents the melanin content value of each subject during each test.

The smaller the value, the more obvious the whitening effect of the eye cream of the invention is relative to the blank group.

Figure 2:
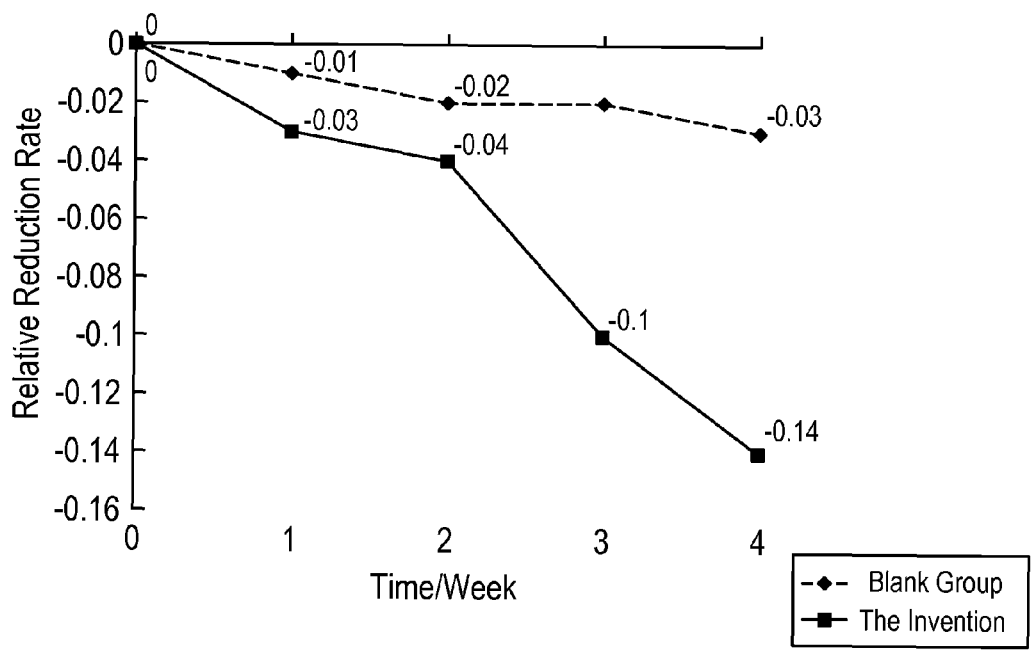
FIG. 2 shows relative changes of melanin after the invention is used.

Result: Analysis results are detailed in FIG. 2.

1. The eye cream has obvious whitening effect after use.

2. The data change of melanin relative to initial value shows a downtrend below the baseline after the use of the eye cream, which shows that the content of melanin is obviously lower relative to initial value after the use of the eye cream.

(III) Comparison of Relative Change Rate of Melanin

Relative reduction rate of melanin=(the melanin of the invention group $T_n$–the melanin of the blank group $T_n$)/the melanin of the blank group $T_n$.

The smaller the value, the more obvious the whitening effect of the test sample is relative to the blank sample.

Figure 3:
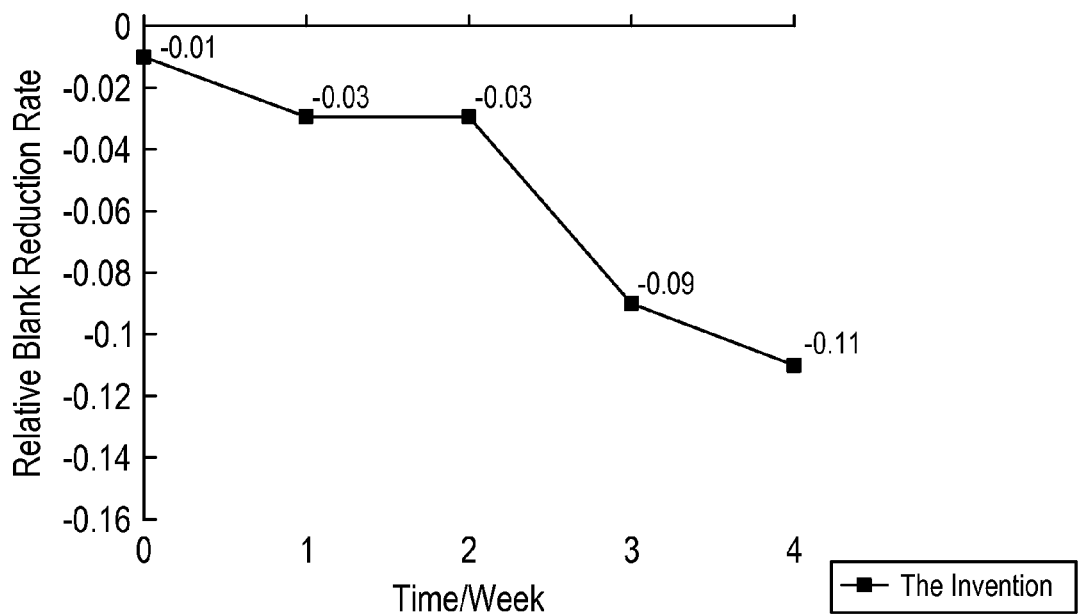
FIG. 3 shows changes of melanin after the invention is used relative to a blank sample.

Result: Analysis results are detailed in FIG. 3.

The relative reduction value data of melanin fluctuats below the baseline as a whole and shows a downtrend, which shows that the whitening effect is obvious after the use of the eye cream.

(IV) Changes of Skin Lightness (L)

L represents skin lightness. The bigger the lightness value, the color tends to be white.

Figure 4:
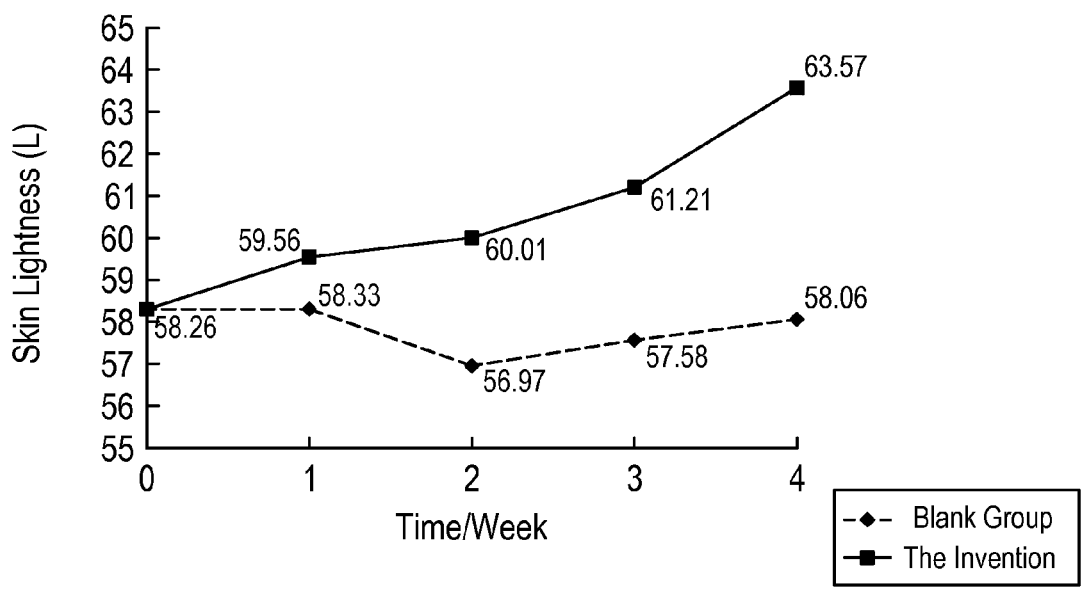
FIG. 4 shows changes of skin lightness (L) after the invention is used.
Figure 5:
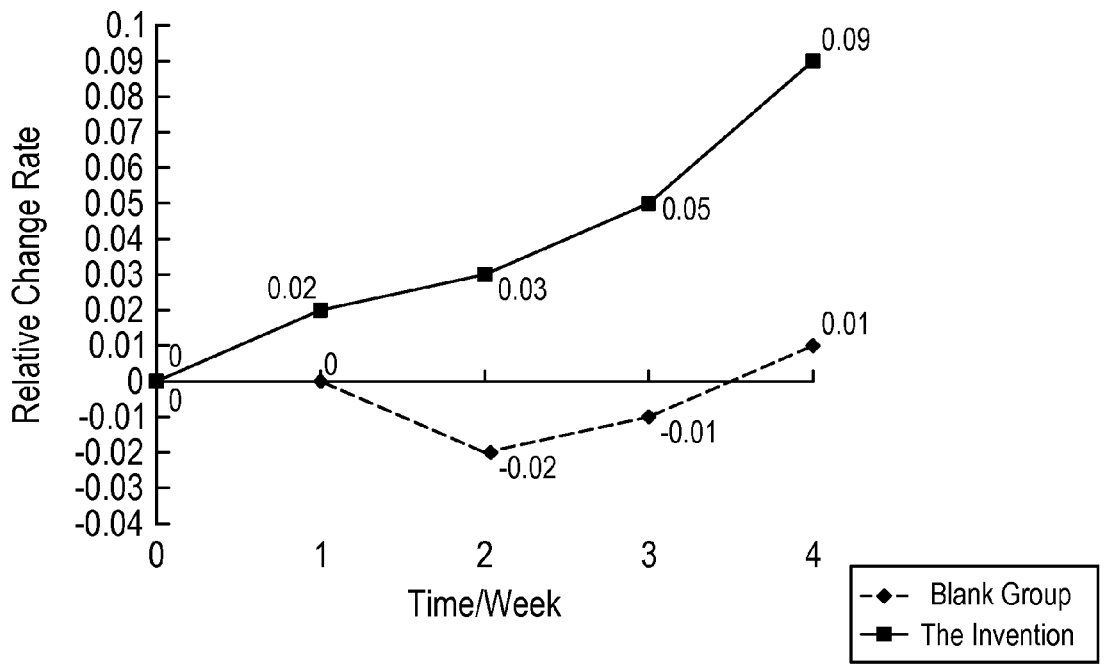
FIG. 5 shows changes of skin lightness (L) after the invention is used relative to the initial value.
Figure 6:
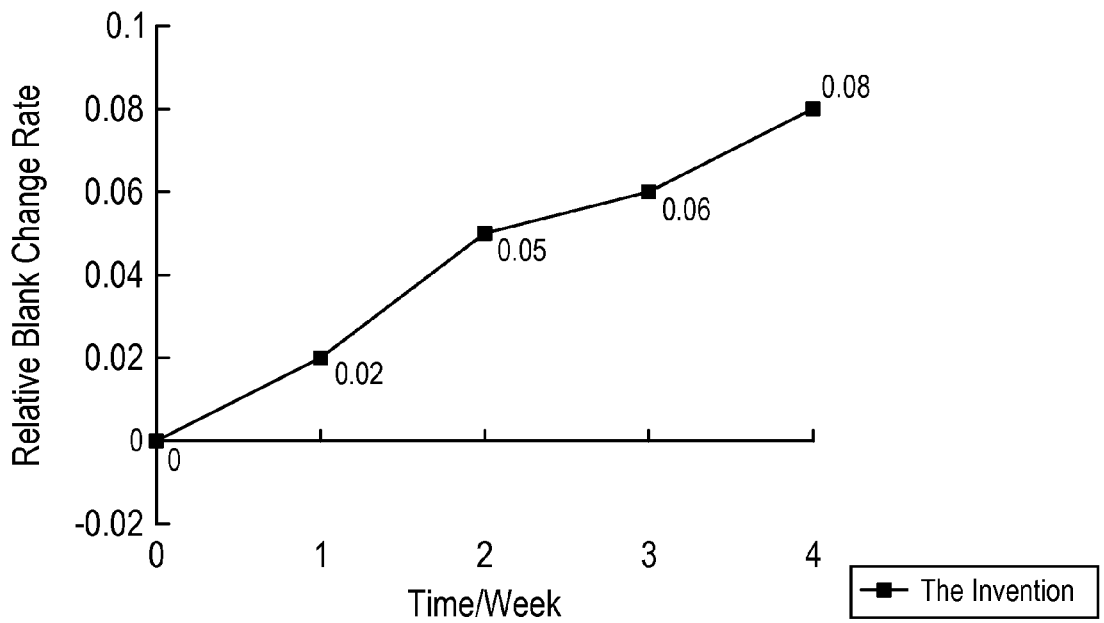
FIG. 6 shows a relative change rate of skin lightness (L) after the invention is used.

Change value of L relative to initial value=(weekly measured value of L–initial measured value of L)/initial measured value of L Relative change rate of L=(the L of the invention group–the L of the blank group)/the L of the blank group Result: Analysis results are detailed in FIGS. 4, 5 and 6.

1. Experimental data are analyzed significantly by at test method. The results show that: there is a significant difference in the skin lightness starting from the second week after the use of the eye cream ($p<0.05$).

2. Data obtained after the use of the eye cream at different time are analyzed significantly by at test method. The results show that: there is a significant difference between the test group and the blank group starting from the second week ($p<0.05$).

3. The eye cream has the effect of significantly increasing the skin lightness after use.

II. Evaluation Results of Anti-Aging Efficacy

Method: There are totally 32 subjects. Specific gender composition and age composition are determined randomly.

The invention group refers to the eye skin of a subject who applies the eye cream of any embodiment of the invention, and the blank group refers to the eye skin of a subject who does not apply the eye cream.

Changes of skin texture:

Reduction rate=(the data of the invention group $T_n$–the initial value $T_0$)/the initial value $T_0$ Relative reduction rate=(the data of the invention group $T_n$–the data of the blank group $T_n$)/the data of the blank group $T_n$ 1. Skin roughness (SR)

It is a difference value between a maximum gray peak and a minimum gray peak on a straight line in all the profiles of the skin. The parameter is the maximum height of skin surface roughness.

Figure 7:
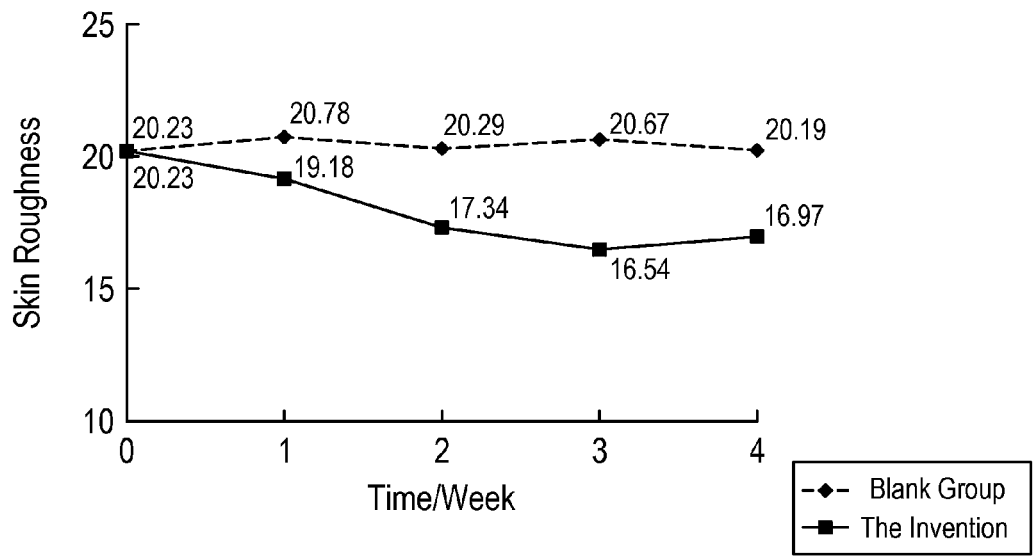
FIG. 7 shows changes of skin roughness after the invention is used.
Figure 8:
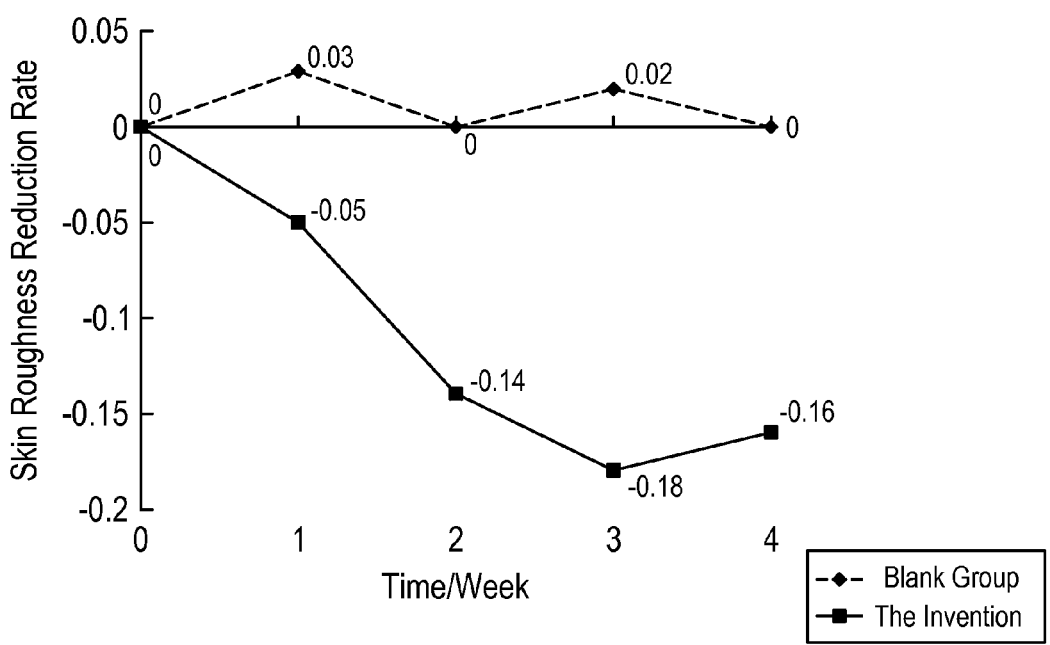
FIG. 8 shows reduction rate changes of skin roughness after the invention is used.
Figure 9:
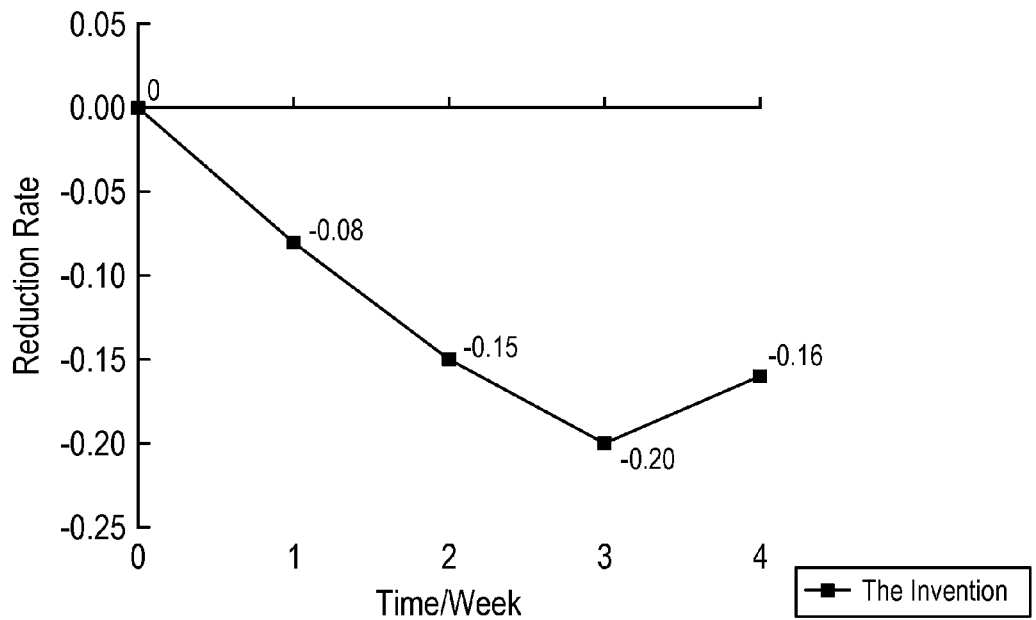
FIG. 9 shows relative reduction rate changes of skin roughness after the invention is used.

Result: Analysis results are detailed in FIGS. 7, 8 and 9.

(1) The skin roughness steadily reduces after the use of the eye cream of the invention, i.e. the skin roughness significantly decreases.

(2) Relative to the initial value, there is a significant difference relative to the blank group starting from the second week after the use of the eye cream ($p<0.05$).

(3) The eye cream has the effect of significantly improving the skin roughness after use.

2. Skin average roughness (SAR)

Figure 10:
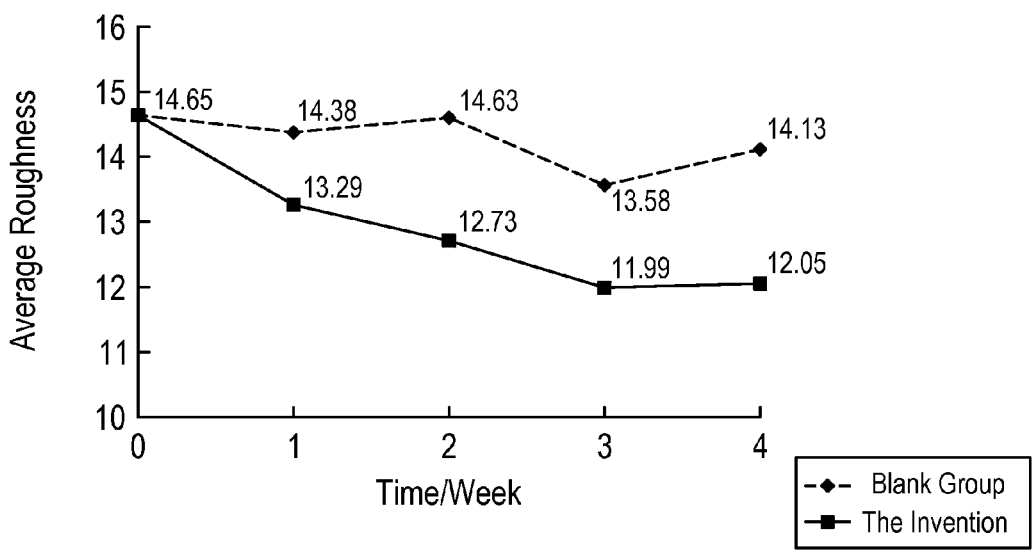
FIG. 10 shows changes of skin average roughness after the invention is used.
Figure 11:
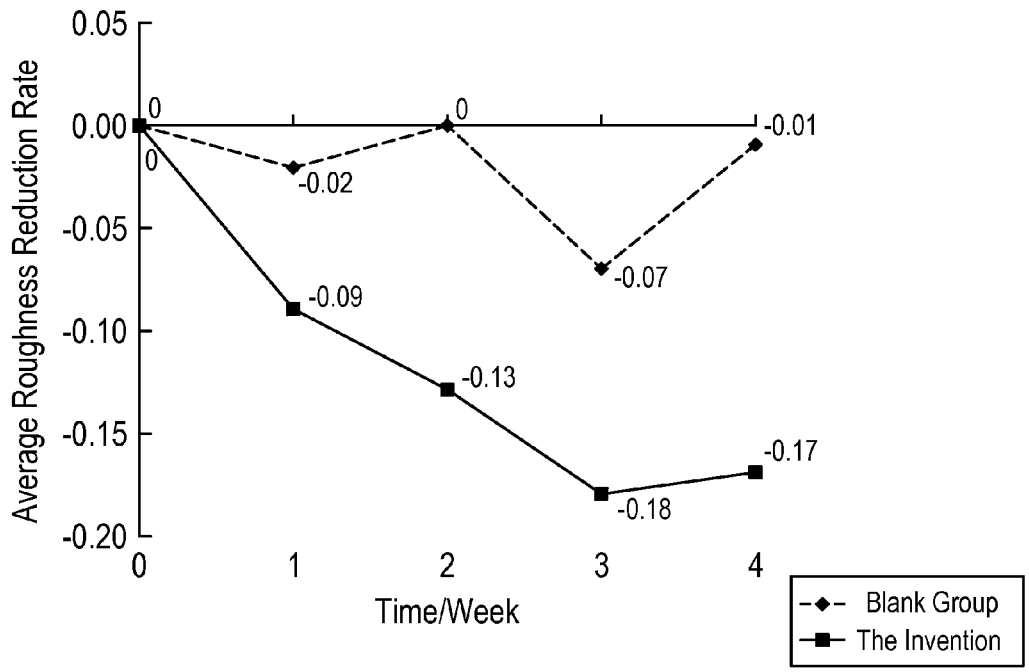
FIG. 11 shows reduction rate changes of skin average roughness after the invention is used.
Figure 12:
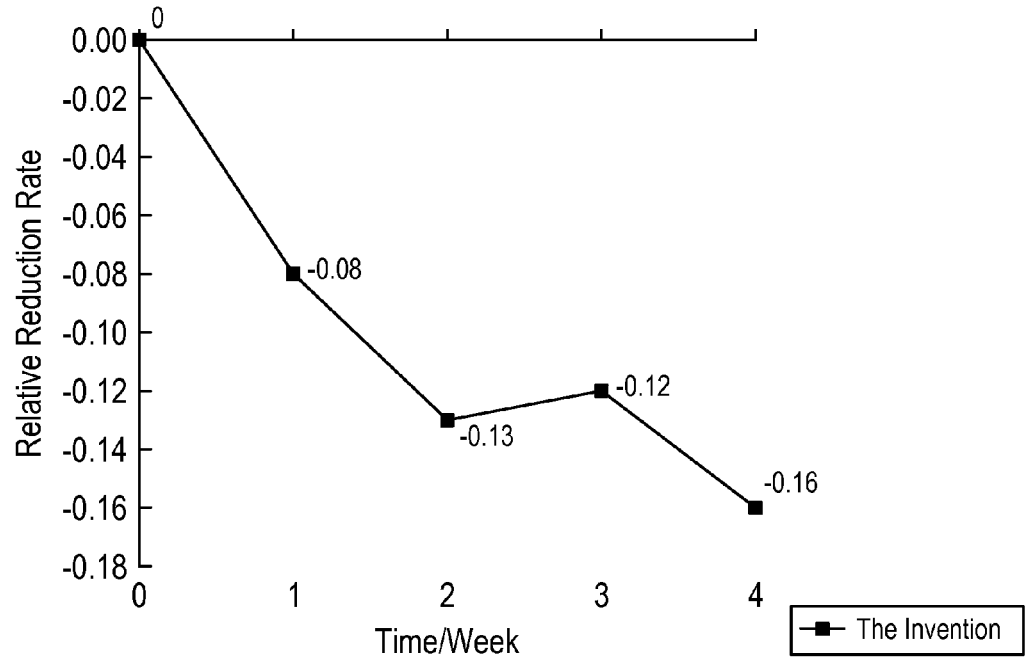
FIG. 12 shows relative reduction rate changes of skin average roughness after the invention is used.

It is an arithmetic mean of skin wheal contours above and below the baseline of target skin. That is to say, an ultimate profile is divided into 5 equal pieces based on a length, a difference value, i.e. skin roughness, between a skin wheal contour above the baseline (maximum gray value) and a skin wheal contour below the baseline (minimum gray value) of each segment is determined first, then a roughness mean (arithmetic mean) within the length baseline is determined, i.e. skin average roughness. The parameter is closely related to the number, size and depth of skin wrinkles Result: Analysis results are detailed in FIGS. 10, 11 and 12.

(1) The skin average roughness steadily reduces after the use of the eye cream, i.e. the skin average roughness significantly decreases.

(2) Relative to the initial value, the reduction rate of average roughness is better than that of the blank group, and there is a significant difference starting from the second week after the use of the eye cream ($p<0.05$).

(3) The eye cream has the effect of significantly improving the skin average roughness after use.

3. Maximum Roughness (MR)

It refers to the maximum value between the adjacent maximum gray peak and minimum gray peak on the straight line in the cut skin section. It is equivalent to the maximal wrinkle in the skin texture.

Figure 13:
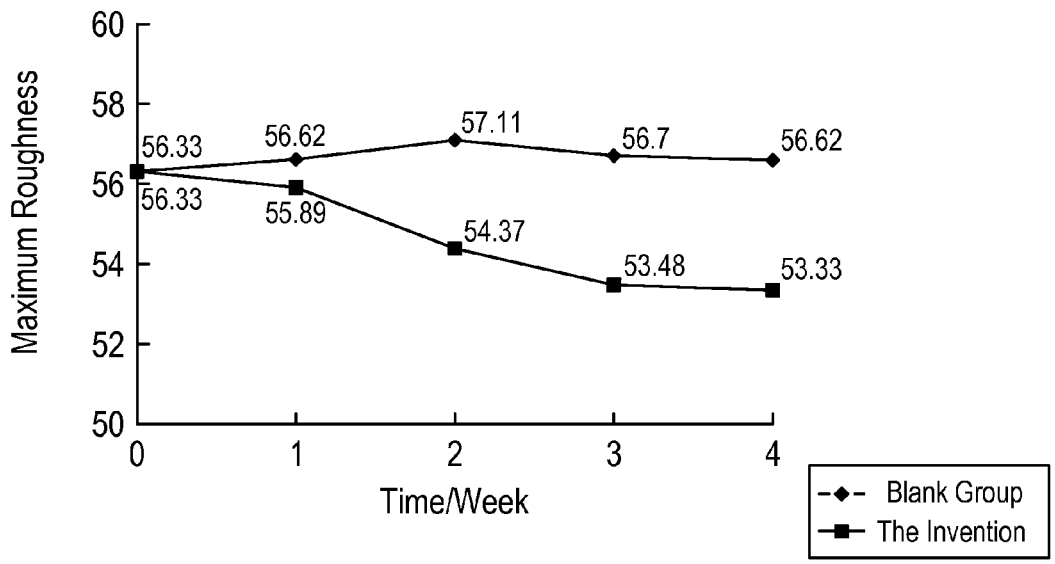
FIG. 13 shows changes of skin maximum roughness after the invention is used.
Figure 14:
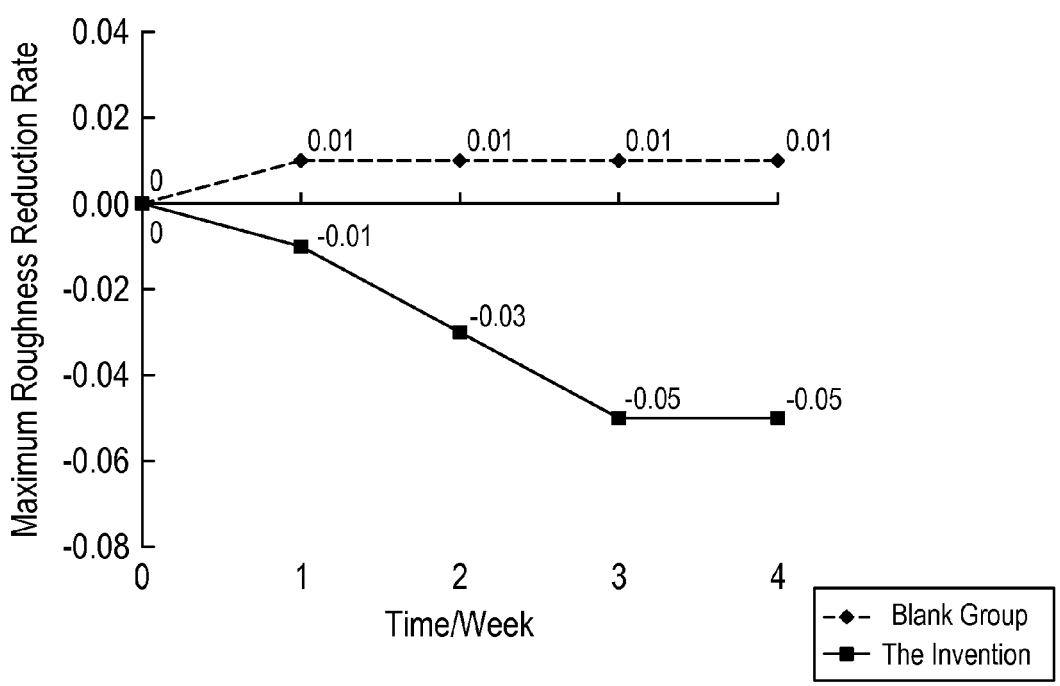
FIG. 14 shows reduction rate changes of skin maximum roughness after the invention is used.
Figure 15:
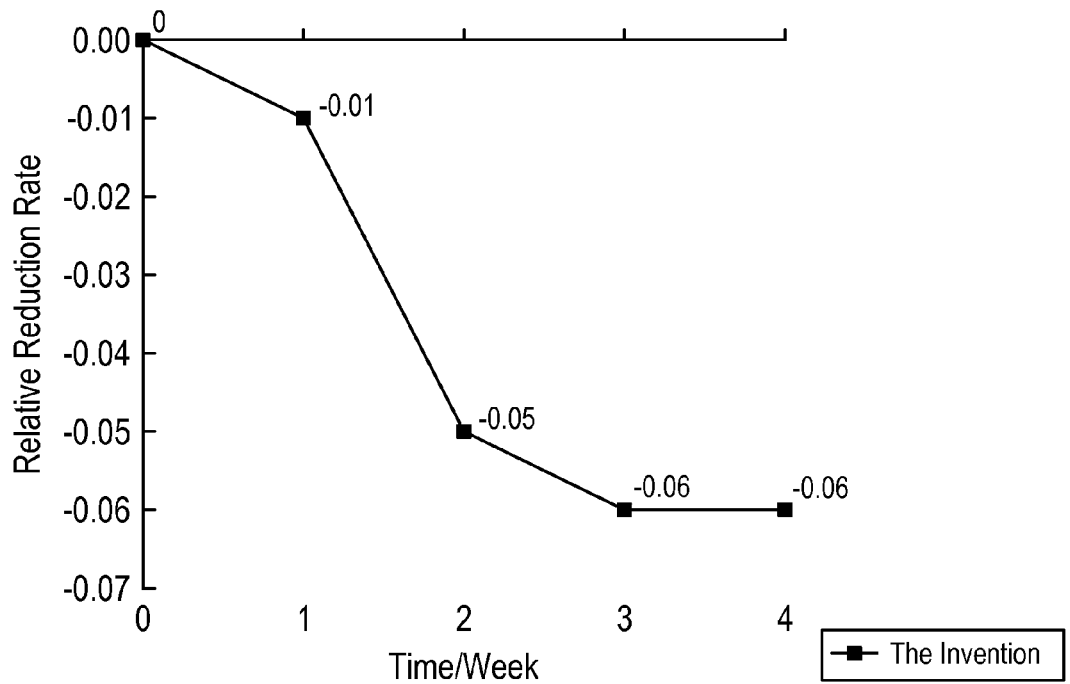
FIG. 15 shows relative reduction rate changes of skin maximum roughness after the invention is used.

Result: Analysis results are detailed in FIGS. 13, 14 and 15.

(1) The skin maximum roughness steadily reduces after the use of the eye cream, i.e. the skin maximum roughness significantly decreases.

(2) The reduction rate of skin maximum roughness is obviously better than that of the blank group, and there is a significant difference starting from the second week after the use of the eye cream ($p<0.05$).

4. Skin Smoothness Depth (SSD)

It refers to the average distance between two peaks of the highest point of skin wheal (maximum gray value curve) and the lowest point of skin ditch (minimum gray value curve), i.e. the average distance between the highest point of the contour line of the skin surface and the lowest point of the bottom line of skin wrinkle.

Figure 16:
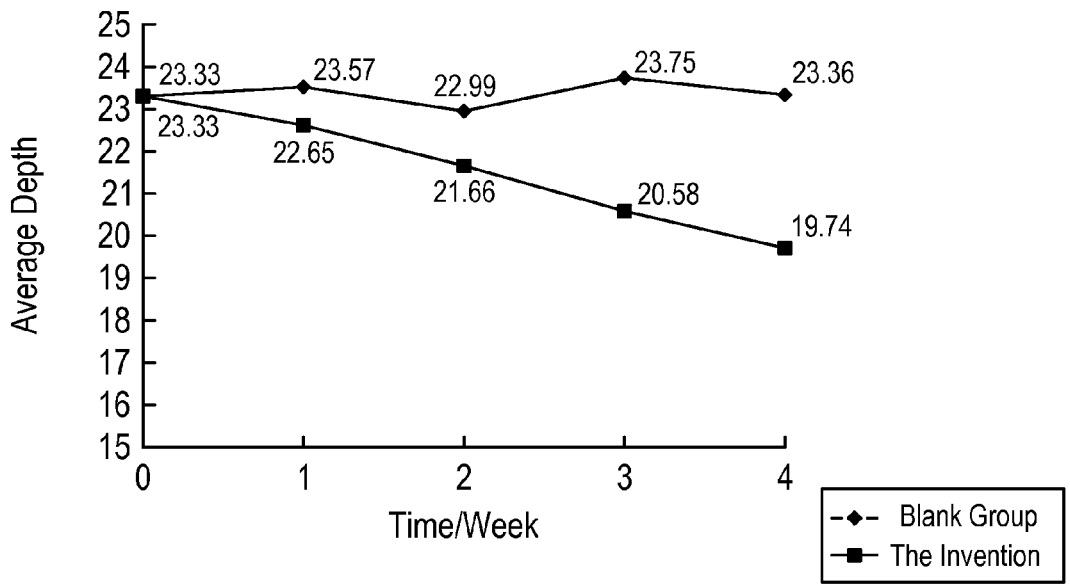
FIG. 16 shows changes of skin smoothness depth after the invention is used.
Figure 17:
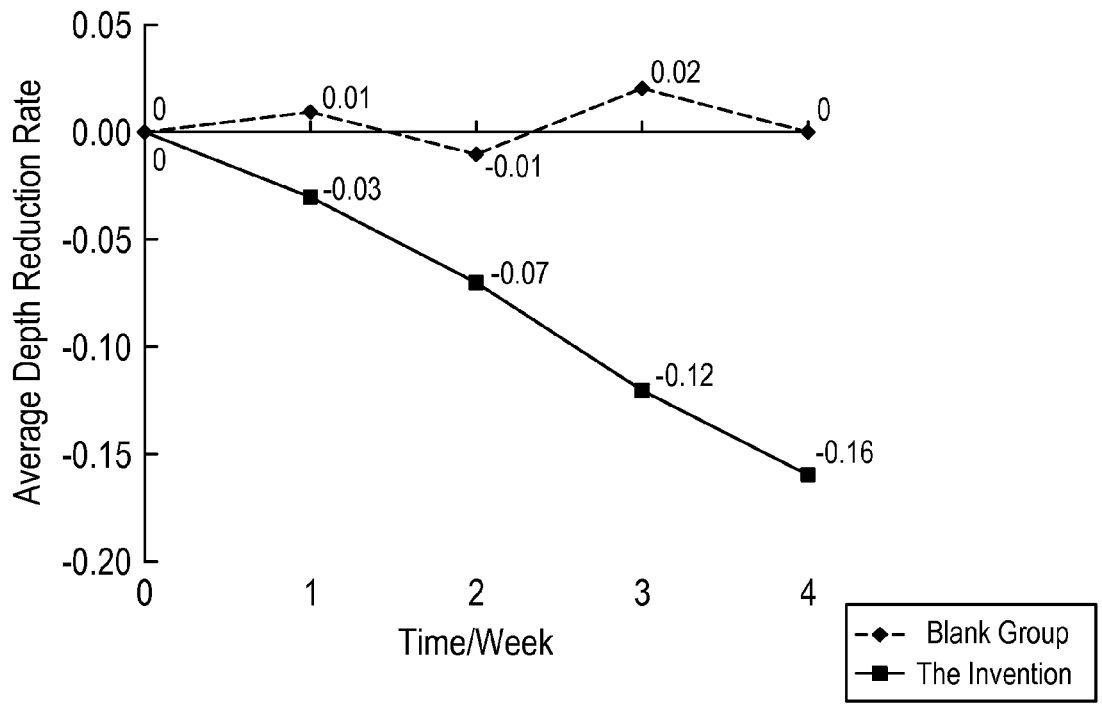
FIG. 17 shows reduction rate changes of skin smoothness depth after the invention is used.
Figure 18:
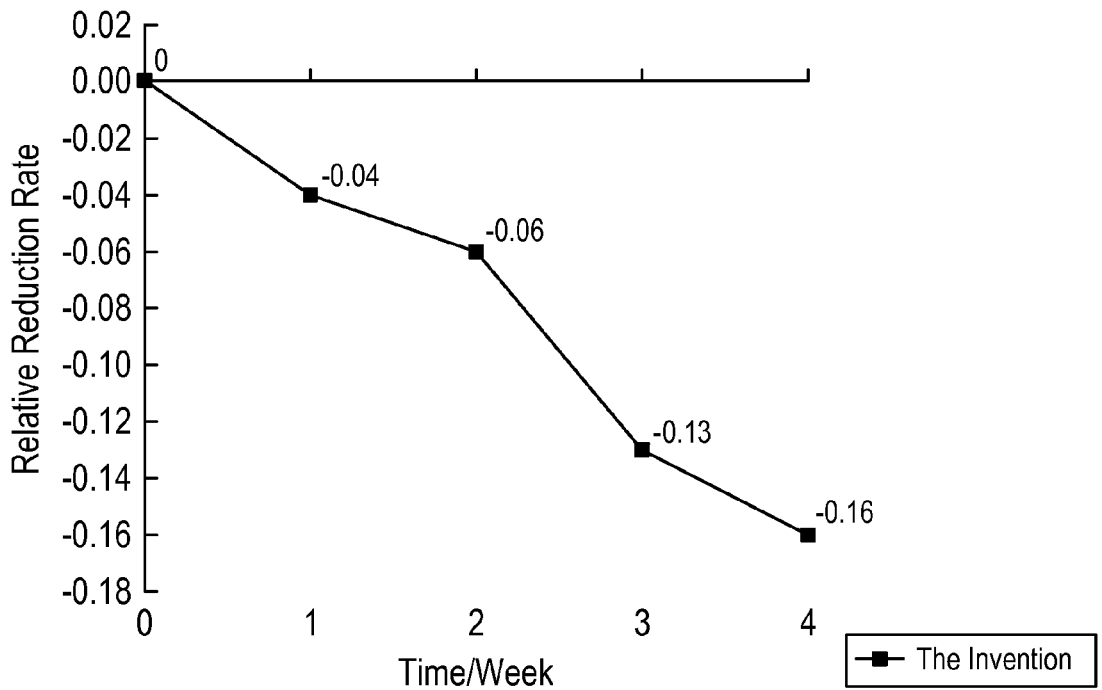
FIG. 18 shows relative reduction rate changes of skin smoothness depth after the invention is used.

Result: Analysis results are detailed in FIGS. 16, 17 and 18.

(1) The skin smoothness depth steadily reduces after the use of the eye cream, i.e. the skin smoothness depth significantly decreases.

(2) The reduction rate of skin smoothness depth is improved better than the blank group, and there is a significant difference starting from the third week after the use of the eye cream ($p<0.05$).

5. Arithmetic average roughness (AAR)

It refers to an average distance from the gray curve on the straight line of target skin to average gray value, i.e. an arithmetic mean of absolute values of each point on the contour line of the tested skin surface to the distance of contour midline within the range of straight length.

Figure 19:
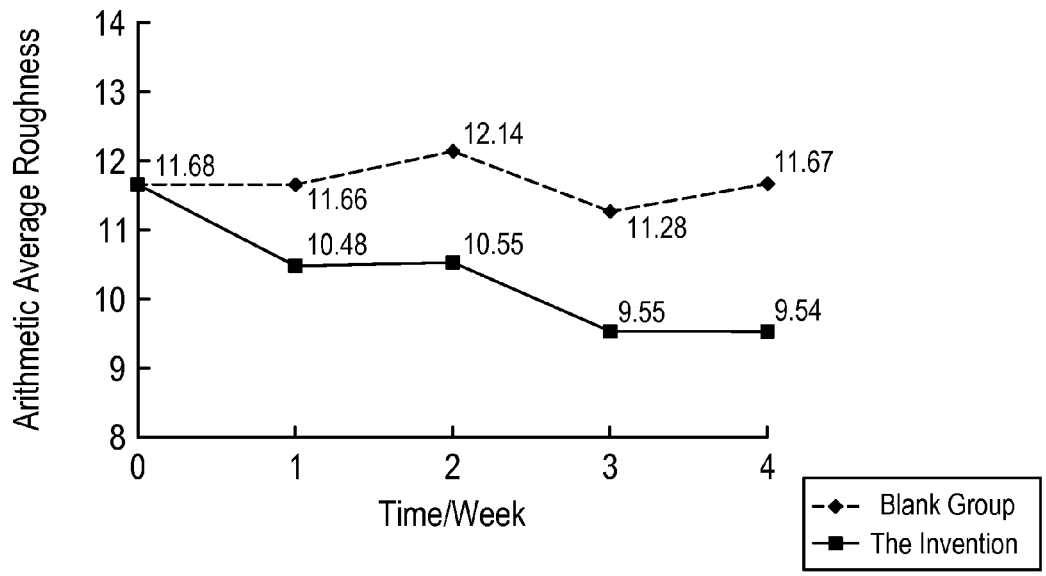
FIG. 19 shows changes of arithmetic average roughness after the invention is used.
Figure 20:
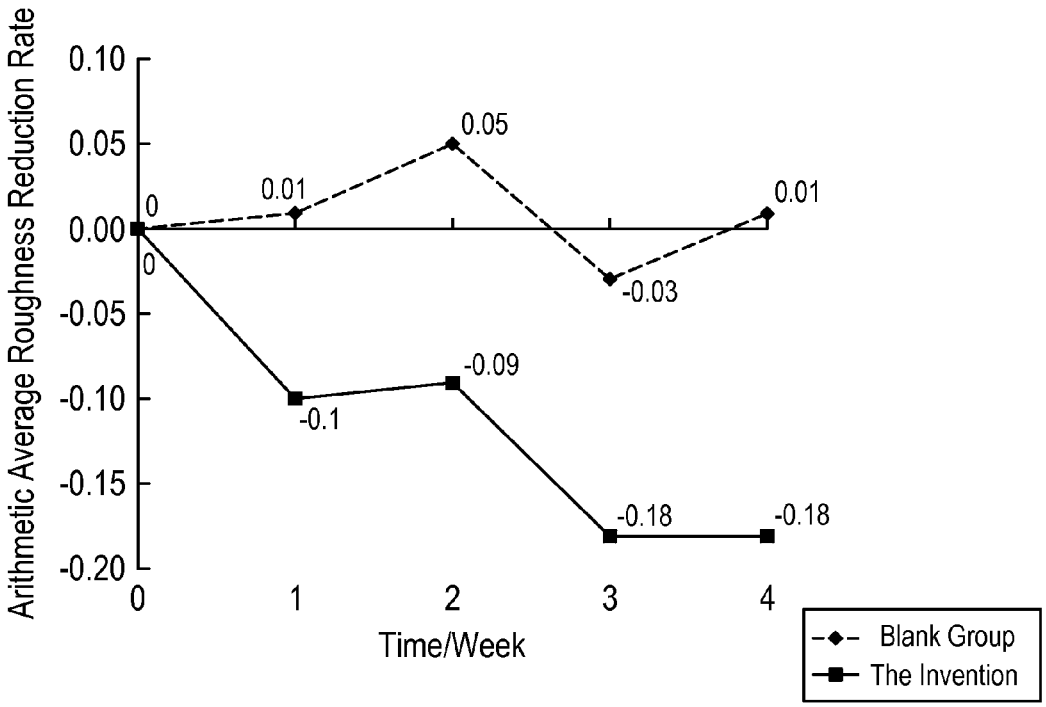
FIG. 20 shows reduction rate changes of arithmetic average roughness after the invention is used.
Figure 21:
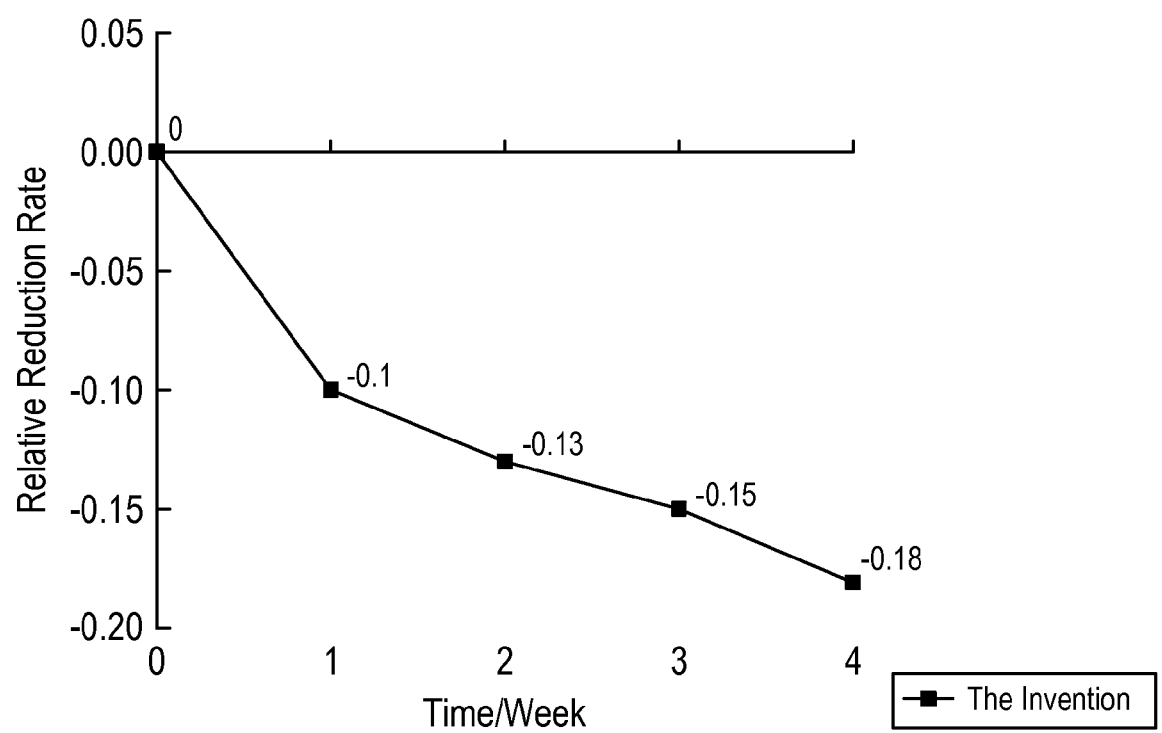
FIG. 21 shows relative reduction rate changes of arithmetic average roughness after the invention is used.

Result: Analysis results are detailed in FIGS. 19, 20 and 21.

(1) The skin arithmetic average roughness steadily reduces after the use of the eye cream, i.e. the skin arithmetic average roughness significantly decreases.

(2) The reduction rate of skin arithmetic average roughness is improved better than the blank group, and there is a significant difference starting from the second week after the use of the eye cream ($p<0.05$).

III. Rabbit Acute Eye Stimulation Test

Material and Method:

1. Test substance: The eye cream of any embodiment of the present invention.

2. Animal. 4 conventional rabbits, half male and half female with body weight of 2.2-2.6 kg, offered by the Experimental Animal Center of Hubei Province. The production license number of experimental animal is SCXK (Hubei) 2008-0005, and the certification number of experimental animal is No. 00000912. The animals are observed for 3 days before being fed with test samples, meeting the requirements of the test.

3. Experimental Method 3.1 Dose and group: The test consists of an eye cream group of the invention and a control group. The control group does not receive any treatment. Four rabbits are tested with intra-individual left/right eyes self control method. The given amount of the eye cream of the invention is 0.1 ml/rabbit.

3.2 Selection of test rabbits and preparation before test: Rabbits, eyes of which contain no secretions, cornea and conjunctiva of which are normal in visual observation, are selected. The cornea is inspected with 1% of fluorescein sodium eye drops 20 h before test. If four rabbits are normal, they can be used for the test.

3.3 Preparation of eye cream extract of the invention: Stock solution is directly used for the test, shaken well before test.

3.4 Treatment of test substance: The test rabbits are fixed in a rabbit fixing box. The lower eyelids of the right eyes of the test rabbits are pulled open, 0.1 ml of the eye cream extract of the invention is dropped into the conjunctival sac, and the upper and lower eyelids passively keep closed for 1 second. The left eyes do not receive any treatment as self control.

3.5 Observation of eye stimulation reaction: The left and right eyes of the rabbits are inspected 1 h, 24 h, 48 h and 72 h after the test substance is dropped, and the stimulation reactions of conjunctiva, cornea and iris are graded according to the grading standard of China's Hygienic Specifications for Cosmetics (Edition 2007).

Inspection with fluorescein sodium: The left and right eyes of the rabbits are inspected with fluorescein sodium 20 h before the test substance is given and 24 h after the test substance is given. Inspection method: 1% of fluorescein sodium solution is dropped into the eyes of the test rabbits, the eyes passively keep closed for about 10 seconds, then washed with normal saline; the cornea is checked whether there are spots colored by fluorescein sodium to judge whether the cornea is damaged.

4. Results:

After 0.1 ml of the eye cream extract of the invention is dropped into the right eyes of the test rabbits, all the four test rabbits close their eyes, without obvious secretion and obvious edema. The eye stimulation reactions at each time point are shown in the following table.

TABLE 1

Results of test substance on rabbit acute eye stimulation test

| | | \multicolumn{8}{c}{Eye stimulation reaction score} | | | | | | | |
|---|---|---|---|---|---|---|---|---|---|
| | | 1 h | | 24 h | | 48 h | | 72 h | |
| Animal No. | Position | Sample | Control | Sample | Control | Sample | Control | Sample | Control |
| 1 | Conjunctiva | 0 | 0 | 0 | 0 | 0 | 0 | 0 | 0 |
| | Iris | 0 | 0 | 0 | 0 | 0 | 0 | 0 | 0 |
| | Cornea | 0 | 0 | 0 | 0 | 0 | 0 | 0 | 0 |
| 2 | Conjunctiva | 0 | 0 | 0 | 0 | 0 | 0 | 0 | 0 |
| | Iris | 0 | 0 | 0 | 0 | 0 | 0 | 0 | 0 |
| | Cornea | 0 | 0 | 0 | 0 | 0 | 0 | 0 | 0 |
| 3 | Conjunctiva | 0 | 0 | 0 | 0 | 0 | 0 | 0 | 0 |
| | Iris | 0 | 0 | 0 | 0 | 0 | 0 | 0 | 0 |
| | Cornea | 0 | 0 | 0 | 0 | 0 | 0 | 0 | 0 |
| Class of stimulation reaction | | | | \multicolumn{2}{c}{non-stimulating} | | | | |

Experimental conditions: no washing

IV. Many Skin Stimulation Tests of the Eye Cream on Rabbits

Material and Method:

1. Test substance: The eye cream of any embodiment of the invention.
2. Animal. 4 conventional rabbits, half male and half female with body weight of 2.2-2.6 kg, offered by the Experimental Animal Center of Hubei Province. The production license number of experimental animal is SCXK (Hubei) 2008-0005, and the certification number of experimental animal is No. 00000912. The animals are observed for 3 days before being fed with test samples, meeting the requirements of the test.
3. Experimental Method 3.1 The test consists of a test sample group and a normal saline control group. The normal saline control is an intra-individual left/right self control method, a total of four rabbits.

3.2 The given amount of the test sample: 0.5 g of test sample is applied to each rabbit.

3.3 Selection of test rabbits and preparation before test: Both sides of the vertebra of the rabbits are dehaired by a battery powered shaver 24 h before test within a range of 3 cm×3 cm at left and right. The skin of hairless area is inspected carefully for damage caused by dehairing before the test sample is given. Damaged skin is not appropriate for test.

3.4 Preparation of test sample: The test sample is a cream. It is directly applied onto the skin for carrying out many skin stimulation tests; 0.5 g of test sample is applied to each rabbit accurately.

3.5 Giving method of test sample: The test rabbits are fixed in a rabbit fixing box; 0.5 g of test sample is applied onto the dehaired skin on the right side, with applying area of 2.5×2.5 $cm^2$. The test sample is applied once a day, and continuously applied for 14 days. Starting from the second day, the hair is removed before applying, residual test sample is cleared with warm water from the skin. The result is observed after 1 hour, and graded according to the grading standard of Hygienic Specifications for Cosmetics (Edition 2007); 0.5 ml of normal saline is applied to the left control area. The test method of the control area is the same as that of the right test area. The applying time is 23 hours. The test rabbits are put back to a rabbit rearing cage for raising after applying.

3.6 Test Observation Index

Residual test sample is cleared with warm water starting from the second day. The result is observed after 1 hour, and graded according to the grading standard of Hygienic Specifications for Cosmetics (Edition 2007).

Test Results

After observation, the animals do not exhibit systemic poisoning. The skin also has no obvious erythema and edema. Results are shown in the following table:

TABLE 2

Results of the eye cream of the invention on many rabbit skin stimulation tests

| | | \multicolumn{6}{c}{Skin stimulation reaction score} | | | | | |
|---|---|---|---|---|---|---|---|
| | The number of | \multicolumn{3}{c}{Sample} | \multicolumn{3}{c}{Control} | |
| Applying days | animals (ones) | Erythema | Edema | Total score | Erythema | Edema | Total score |
| 1 | 4 | 0 | 0 | 0 | 0 | 0 | 0 |
| 2 | 4 | 0 | 0 | 0 | 0 | 0 | 0 |
| 3 | 4 | 0 | 0 | 0 | 0 | 0 | 0 |
| 4 | 4 | 0 | 0 | 0 | 0 | 0 | 0 |
| 5 | 4 | 0 | 0 | 0 | 0 | 0 | 0 |
| 6 | 4 | 0 | 0 | 0 | 0 | 0 | 0 |
| 7 | 4 | 0 | 0 | 0 | 0 | 0 | 0 |
| 8 | 4 | 0 | 0 | 0 | 0 | 0 | 0 |
| 9 | 4 | 0 | 0 | 0 | 0 | 0 | 0 |
| 10 | 4 | 0 | 0 | 0 | 0 | 0 | 0 |
| 11 | 4 | 0 | 0 | 0 | 0 | 0 | 0 |
| 12 | 4 | 0 | 0 | 0 | 0 | 0 | 0 |
| 13 | 4 | 0 | 0 | 0 | 0 | 0 | 0 |
| 14 | 4 | 0 | 0 | 0 | 0 | 0 | 0 |

TABLE 2-continued

Results of the eye cream of the invention on many rabbit skin stimulation tests

| | | Skin stimulation reaction score | | | | | |
|---|---|---|---|---|---|---|---|
| | | Sample | | | Control | | |
| Applying days | The number of animals (ones) | Erythema | Edema | Total score | Erythema | Edema | Total score |
| Score mean value of each animal within 14 days | | 0 | 0 | 0 | 0 | 0 | 0 |
| Score mean value of each animal every day | | 0 | 0 | 0 | 0 | 0 | 0 |
| Class of stimulation intensity | | | | non-stimulating | | | |

V. Stimulation Test Results

Experimental method: Refer to ECVAM DB-ALM: INVITTOX protocol; Red Blood Cell Test System INVITTOX n° 37, hereinafter referred to as RBC test system.

The basic principle of the RBC test system is to determine the damage on the cell membrane caused by chemicals and the change of cell membrane permeability resulted from it. The damage degree of the cell membrane, which is directly related to the stimulation of a product, is evaluated through determining the amount of hemoglobin leaked from red blood cells.

The absorbance of red blood cell suspension after exposure to the chemicals is determined by spectrophotometric method, then the hemolysis rate and HSO value (i.e. the concentration value of the test substance, 50% of red blood cells of which develop hemolysis) can be calculated. The HSO value and the results of two grading standards in Draize test, i.e. the maximum average Draize total score (MAS) and the 24 h after application and scores of composition parameters (cornea, conjunctiva and iris) thereof are subjected to correlation analysis to show good consistency. At the same concentration, the higher the hemolysis rate of the sample is, the stronger the stimulation of the sample is.

The stimulation ratio of each sample is as shown in the following table relative to SDS after the comparison of the SDS stimulation ratio:

TABLE 3

Stimulation ratio of samples

| No. | Sample | Stimulation ratio |
|---|---|---|
| 0 | SDS control substance | 100% |
| 1 | The eye cream of the invention | 7.23% |

(1) At a low concentration (an addition concentration of $80 \times 10^{-5}$), the hemolysis rate of the invention is very low, and the eye cream sample is less likely to damage the cell membrane, which proves that the eye cream has no strong stimulation in the RBC test system.

(2) At a high concentration, e.g. at the maximum test concentration (an addition concentration of $640 \times 10^{-5}$) of the test system, the hemolysis rate of the invention is 7.23%. It proves that the control substance of the invention and the sample have no strong stimulation in the RBC test system.

VI. Experimental Results of Human Body Patch Test

Experimental process: There are totally 30 subjects. Specific gender composition and age composition are determined randomly (meeting the inclusion and exclusion criteria of Diagnostic Criteria and Principles of Management of Contact Dermatitis Induced by Cosmetics). Acceptable patch materials are selected, the sample is put into a patch tester after being infiltrated with filter paper, and control holes are used as a blank control (any substance is not placed). The eye cream sample of the invention and the blank control are pasted at forearms of the subjects, and evenly applied onto the skins by gently pressing with palm, lasting for 24 h. The skin reaction is observed at an interval of 30 min after the patch tester is removed and indentation disappears. The skin reaction is again respectively observed at 24 h and 48 h after the patch test.

Judgment Standard:

Classified judgment is carried out according to Diagnostic Criteria and Principles of Management of Contact Dermatitis Induced by Cosmetics: the test position without reaction is judged as (0), the skin with light erythema is judged as (1), the skin with erythema, infiltration or papule is judged as (2), the skin with edematous erythema or papule is judged as (3), and the skin with significant red swelling, papule or bulla is judged as (4).

When more than 2 cases develop the second class adverse cutaneous reactions, or 1 case develops the third class adverse cutaneous reactions or above class in 30 cases, it is judged that the test substance has adverse reactions to human body.

Specific result evaluation is as shown in the following table:

TABLE 4

| No reaction | Light erythema | Erythema, infiltration or papule | Edematous erythema or papule | Significant red swelling, papule or bulla |
|---|---|---|---|---|
| 30 | 0 | 0 | 0 | 0 |

The experimental results show that the eye cream provided by the invention has no adverse reaction to human body.

The above embodiment is only a preferred embodiment given to fully describe the invention, but the protection scope of the invention is not limited herein. Equivalent replacements or transformations made by those skilled in the art on the basis of the invention shall fall within the protection scope of the invention. The protection scope of the invention shall be subject to the claims.

The invention claimed is:

1. An eye cream, wherein the eye cream comprises the following components in amounts of parts by weight:
    2-16 parts by weight of pearl;
    0.2-2 parts by weight of borax;
    10-28 parts by weight of Vitamin E (VE);
    0.005-0.05 parts by weight of muscone;
    0.2-3 parts by weight of borneol;
    30-90 parts by weight of a mixture of sodium metmethyl parahydroxybenzoate, propyl parahydroxy benzoate,

*Capsicum frutensense* fruit extract, *Citrus grandis* fruit extract, *Ruscus aculeatus* root extract, *Equisetum arvense* extract, *Glycyrrhiza glabra* extract, ascorbyl methysilanol pectinate, methylsilanol hydroxyproline asparte, dimethylsilanol hyaluronate, aminoethyl phosphinic acid, propylene glycol, butylene glycol, PEG-35 castor oil, and water;
0.05-2 parts by weight of zinc carbonate hydroxide;
470-700 parts by weight of de-ionized water;
45-75 parts by weight of propylene glycol;
10-40 parts by weight of cetearyl alcohol;
20-45 parts by weight of petrolatum;
6-25 parts by weight of glyceryl stearate;
40-64 parts by weight of glycerol;
and 7-30 parts by weight of polyacrylamide;
0.1-1 parts by weight of disodium EDTA;
0.2-10 parts by weight of methyl hydroxybenzoate;
70-120 parts by weight of cyclomethicone;
18-40 parts by weight of polydimethylsiloxane;
0.05-2 parts by weight of propyl hydroxybenzoate;
1-14 parts by weight of citric acid;
1-5 parts by weight of DMDM hydantoin;
0.6-3 parts by weight of essence;
1-8 parts by weight of polysorbate-20;
and 1-15 parts by weight of polysorbate-60.

2. An eye cream, wherein the eye cream comprises the following components in amounts of parts by weight:
   2-16 parts by weight of powdered pearl;
   0.2-2 parts by weight of borax;
   10-28 parts by weight of Vitamin E;
   0.005-0.05 parts by weight of muscone;
   0.2-3 parts by weight of borneol;
   30-90 parts by weight of a mixture of sodium methyl parahydroxybenzoate, propyl parahydroxy benzoate, *Capsicum frutensense* fruit extract, *Citrus grandis* fruit extract, *Ruscus aculeatus* root extract, *Equiseturn arvense* extract, *Glycyrrhiza glabra* extract, ascorbyl methysilanol pectinate, methylsilanol hydroxyproline aspartate, dimethylsilanol hyaluronate, aminoethyl phosphinic acid, propylene glycol, butylene glycol, PEG-35 castor oil, water, and
   ethyl alcohol;
   0.05-2 parts by weight of zinc carbonate hydroxide;
   470-700 parts by weight of de-ionized water;
   45-75 parts by weight of propylene glycol;
   10-40 parts by weight of cetearyl alcohol;
   20-45 parts by weight of petrolatum;
   6-25 parts by weight of glyceryl stearate;
   40-64 parts by weight of glycerol;
   and 7-30 parts by weight of polyacrylamide;
   0.1-1 parts by weight of disodium EDTA;
   0.2-10 parts by weight of methyl hydroxybenzoate;
   70-120 parts by weight of cyclomethicone;
   18-40 parts by weight of polydimethylsiloxane;
   0.05-2 parts by weight of propyl hydroxybenzoate;
   1-14 parts by weight of citric acid;
   1-5 parts by weight of DMDM hydantoin;
   06-3 parts by weight of essence;
   1-8 parts by weight of polysorbate-20;
   and 1-15 parts by weight of polysorbate-60.

3. The eye cream of claim 1, wherein the pearl is powdered pearl.

4. A method for preparing the eye cream according to claim 1, comprising the following steps:
   (1) pulverizing pearl and borax respectively, mixing with basic zinc carbonate after sieving with a 100 mesh sieve, grinding and sieving with a 160 mesh sieve, pulverizing mixed powder to 200 mesh by airflow;
   (2) homogenizing the mixed powder obtained in Step (1) with the glycerol and mixing them uniformly;
   (3) taking said amount of de-ionized water and 40~60 parts by weight of propylene glycol, adding them into a homogeneous boiler orderly, uniformly dispersing, heating to 78° C. and preserving heat for subsequent use;
   (4) taking said amount of cetearyl alcohol, white vaseline and glyceryl stearate, adding them into a boiler orderly, heating to 78° C., adding the mixture obtained in Step (2) into the boiler, and uniformly dispersing;
   (5) adding the mixture obtained in Step (4) into the mixture obtained in Step (3), homogenizing them, mixing uniformly and cooling;
   (6) adding said amount of polyacrylamide into the mixture obtained in Step (5) while cooling it to 70° C., vacuumizing them, homogeneously stirring uniformly and cooling;
   (7) cooling the mixture obtained in Step (6) to 50° C., adding said amount of Vitamin E (VE), muscone, propylene glycol solution of borneol and a mixture of sodium methyl parahydroxybenzoate, propyl parahydroxy benzoate, *Capsicum frutensense* fruit extract. *Citrus grandis* fruit extract, *Ruscus aculeatus* root extract, *Equisetum arvense* extract, *Glycyrrhiza glabra* extract, ascorbyl methylsilanol pectinate, methylsilanol hydroxylproline asparte, dimethylsilanol hyaluronate, aminoethyl phophinic acid, propylene glycol, butylene glycol, PEG-35 castor oil, and water into the mixture orderly, homogeneously stirring uniformly, wherein the propylene glycol solution of borneol is obtained by dissolving said amount of borneol in 5-15 parts of propylene glycol;
   (8) cooling the mixture obtained in Step (7) to 37-38° C., stirring it uniformly.

5. A method for preparing the eye cream according to claim 1, comprising the following steps:
   (1) pulverizing pearl and borax respectively, mixing with basic zinc carbonate after sieving with a 100 mesh sieve, grinding and sieving with a 160 mesh sieve, pulverizing mixed powder to 200 mesh by airflow;
   (2) homogenizing the mixed powder obtained in Step (1) with the glycerol and mixing them uniformly;
   (3) taking 457-675 parts by weight of de-ionized water, said amount of disodium EDTA, polysorbate-60 and methyl hydroxybenzoate and 40~60 parts by weight of propylene glycol, adding them into a homogeneous boiler orderly, uniformly dispersing, heating to 78° C. and preserving heat for subsequent use;
   (4) taking said amount of polydimethylsiloxane, cetearyl alcohol, white vaseline, glyceryl stearate, cyclomethicone and propyl hydroxybenzoate, adding them into a boiler orderly, heating to 78° C., adding the mixture obtained in Step (2) into the boiler, and uniformly dispersing;
   (5) adding the mixture obtained in Step (4) into the mixture obtained in Step (3), homogenizing them, mixing uniformly and cooling;
   (6) adding said amount of polyacrylamide into the mixture obtained in Step (5) while cooling it to 70° C., vacuumizing them, homogeneously stirring uniformly and cooling;
   (7) adding said amount of citric acid and 8-15 parts of de-ionized water into the mixture obtained in Step (6) while cooling it to 60° C., vacuumizing them, homogeneously stirring uniformly and cooling;

(8) cooling the mixture obtained in Step (7) to 50° C., adding said amount of Vitamin E (VE), muscone, propylene glycol solution of borneol and a mixture of sodium methyl parahydroxybenzoate, propyl parahydroxy benzoate, *Capsicum frutensense* fruit extract, *Citrus grandis* fruit extract, *Ruscus aculeatus* root extract, *Equisetum arvense* extract, *Glycyrrhiza glabra* extract, ascorbyl methylsilanol pectinate, methylsilanol hydroxyproline asparte, dimethylsilanol hyaluronate, aminoethyl phosphinic acid, propylene glycol, butylene glycol, PEG-35 castor oil, and water into the mixture orderly, homogeneously stirring uniformly, wherein the propylene glycol solution of borneol is obtained by dissolving said amount of borneol in 5-15 parts of propylene glycol;

(9) adding said amount of DMDM hydantoin, 5-10 parts by weight of de-ionized water, said amount of essence and said amount of polysorbate-20 into the mixture obtained in Step (8) while cooling it to 40° C., homogeneously stirring uniformly;

(10) cooling the mixture to 37-38° C., stirring it uniformly.

\* \* \* \* \*